United States Patent
Lopez Escobar

(10) Patent No.: US 7,178,287 B2
(45) Date of Patent: Feb. 20, 2007

(54) PROCEDURE TO INCREASE THE VOLUME OF FRUIT GROWN

(76) Inventor: Nestor Javier Lopez Escobar, Victoria de los Angeles 9, E-04740 Roquetas de Mar (Almeria) (ES)

(*) Notice: Subject to any disclaimer, the term of this patent is extended or adjusted under 35 U.S.C. 154(b) by 0 days.

(21) Appl. No.: 11/038,824

(22) Filed: Jan. 19, 2005

(65) Prior Publication Data

US 2005/0210743 A1    Sep. 29, 2005

Related U.S. Application Data

(63) Continuation of application No. PCT/ES03/00376, filed on Jul. 22, 2003.

(30) Foreign Application Priority Data

Jul. 22, 2002    (ES) ................................ 200201715

(51) Int. Cl.
   *A01G 7/06*    (2006.01)
(52) U.S. Cl. ................................................ 47/58.1 FV
(58) Field of Classification Search ............. 47/1.01 R, 47/47, 89, 58.1 R, 58.1 FV
   See application file for complete search history.

(56) References Cited

U.S. PATENT DOCUMENTS 4,112,616 A    9/1978    Savage 4,193,224 A * 3/1980 Turner .................. 47/1.01 R
4,276,721 A * 7/1981 Turner .................. 47/1.01 R
2005/0210743 A1* 9/2005 Lopez Escobar ....... 47/58.1 FV

FOREIGN PATENT DOCUMENTS

| EP | 1523877 A1 * | 4/2005 |
| WO | WO 00/72660 | 12/2000 |
| WO | WO2004/010768 A1 * | 2/2004 |

OTHER PUBLICATIONS

Oregon State University, Commercial Vegetable Production Guide; Greenhouse Tomato; revised Apr. 24, 2002;□□http://oregonstate.edu/dept/NWREC/tomatogh.html.*

* cited by examiner

*Primary Examiner*—Francis T. Palo
(74) *Attorney, Agent, or Firm*—Sturm & Fix LLP

(57) ABSTRACT

The present invention makes reference to a method of cultivation to improve the fruit crop and is characterised in that it consists of applying pressure, mainly to the base of the floral cluster, making it in the period between the opening of the first flowers and the end of the fattening of the last fruit in order, to thus obtain bigger fruit. The stated pressure must, by preference, be made a short time after the appearance of the first flowers.

Figure 1:
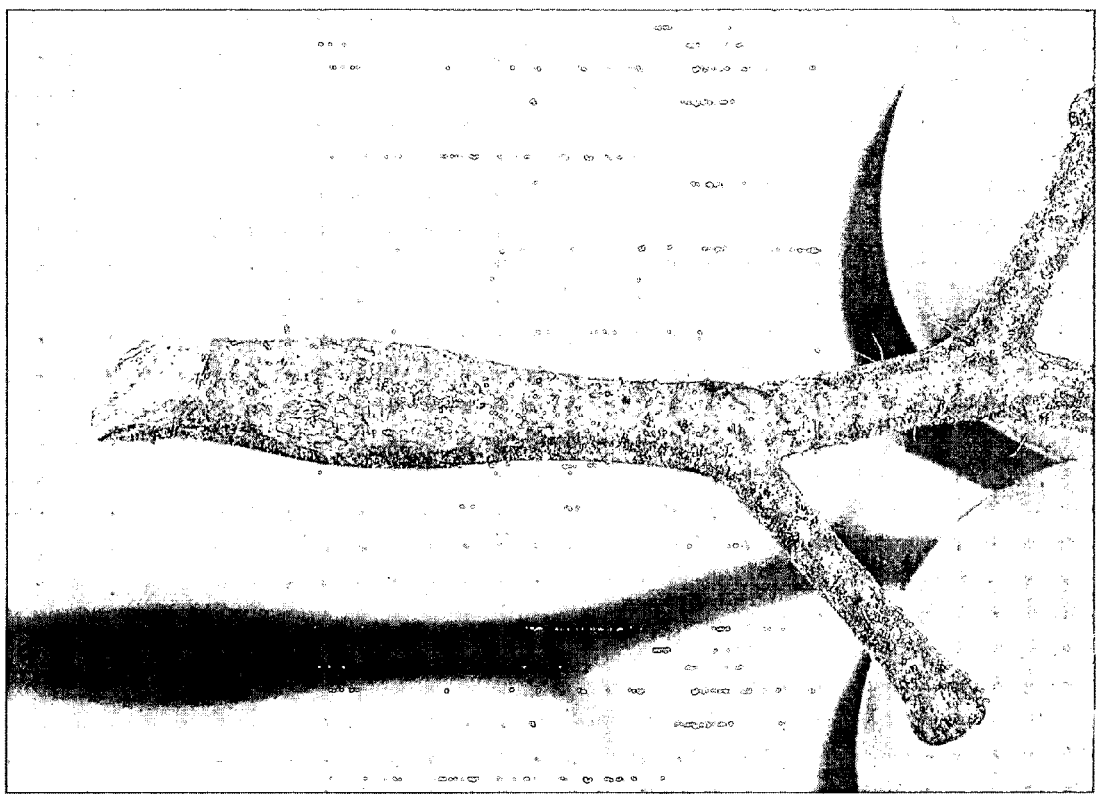

The present invention is applicable to the Solanaceae group of plants.

4 Claims, 2 Drawing Sheets

PROCEDURE TO INCREASE THE VOLUME OF FRUIT GROWN

CROSS REFERENCE TO RELATED APPLICATIONS

This application is a continuation of PCT ES2003/000376 filed Jul. 22, 2003 claiming priority of Application No. ES 200201715 filed Jul. 22, 2002, which is included in its entirety by reference made herein.

OBJECT OF THE INVENTION

The present invention makes reference to a method to increase the calibre of fruit from plants by means of an incision or pressure on any part of a fruit carrying branch, mainly at the base of same. In this way producing the effect on all of the fruit on the branch

1. Field of the Invention

This invention makes reference to the field of agriculture. More specifically it refers to the growing of vegetables and to cultivating techniques in order to improve the fruits obtained.

2. State of the Prior Art

At the present time several methods are known to increase the productivity of the crops of tomatoes, as also with many vegetables, or plants in general. These methods can be classified as follows:

Nutritional: adding natural or synthetic chemical fertilisers so that the plant can obtain more of the nutrients that are available in the soil.

Control of the environment: To control the factors of temperature, light, radiation and humidity in a greenhouse so that the climatic conditions for growth are optimal during the development of the plant.

Hormonal: Hormones are added to the plant and/or to the flower so that the fruit sets and for growth and faster ripening. For example, the application of ANA (Acetic Naphthalene Acid and Acetic Naphtoxic Acid) is common. This product can be added via the irrigation water or via the leaves.

Cultivating tasks: There are certain craft techniques to improve the performance of the plants, the most used consists in tying the clusters so as to prevent the weight of the tomatoes themselves strangling the stalks and by strangulation reducing the amount of sap that reaches the fruit.

The present invention refers to a new method to improve the size of the fruit without the need of adding any external product, but deals with a complementary cultivating technique that is different from all of the existing systems.

DESCRIPTION OF THE INVENTION

The present invention refers to a cultivating technique that consists of making an incision or pressure at the base of the floral cluster (inflorescence) to thus obtain, fruit of a larger size.

The present invention is characterised because, surprisingly, it has been found that by making a cut, mainly longitudinal, or pressure at the base of the floral cluster fruit of greater calibre can be obtained. This cut must break the ducts, but without crossing the whole of the cluster in question. Instead of a cut, pressure can also be applied to the base of the cluster, with the same result of breaking the ducts. The breaking of the structure of the ducts in the stalk must be made from the moment of the formation of the inflorescence, until the end of the fattening of the last fruit, in this way the ducts regenerate themselves and the desired effect is achieved.

By preference the incision or pressure must be carried out a short time after the opening of the flowers.

This effect does not happen in the cucurbit plants, but it does in the Solanaceae such as the tomatoes, peppers or aubergines, amongst others.

Figure 2:

The cut must be made longitudinally, by preference, at the base of the cluster as can be seen in FIG. 1. As can be seen in FIG. 2, the cut made to the stalk (1) produces a fattening in the stalk that does not happen in the stalk that is not treated (2).

The cut or incision can be made with any generally used suitable utensil (blades, knives, pincers, . . . ) or a specific utensil to carry out this procedure.

Without meaning to create a theory, it has been found that the fact of making a cut in the stalk, at the right time, forces the plant to regenerate the damaged ducts in addition to increasing their number. All of this together makes, overall, the amount of sap reaching the fruit greater and, thus, the fruit has more nutrients available to develop into a greater size.

Figure 3A:
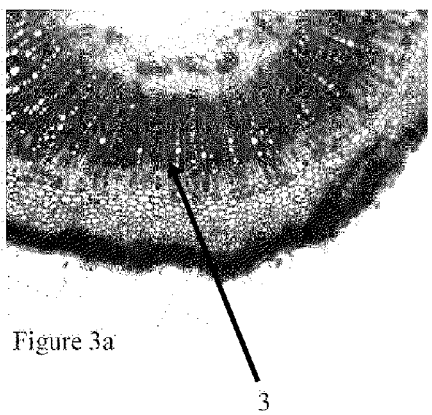
Figure 3B:
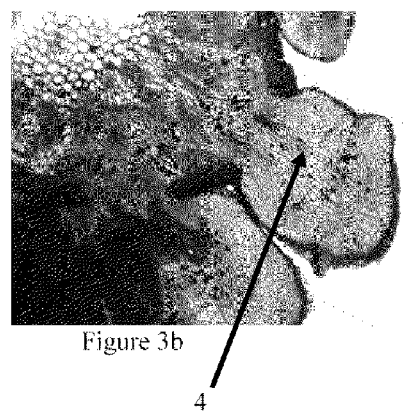

In FIGS. 3a and 3b the structure of the stalk can be seen without having made the cut (FIG. 3a) and once the cut has been made (FIG. 3b). It can be seen from a simple look that in FIG. 3b the stalk of the original structure (3) has fattened with extension (4) in the shape of a drop that contains a large amount of capillary ducts. This increase in the number of capillary ducts enables the amount of sap that reaches the fruit to be greater.

FIGURES

FIG. 1: Detail of the stalk to which the cut has been made and the local fattening produced can be seen.

FIG. 2: Comparison of a stalk with a cut (1) and a stalk without a cut (2), the relative fattening produced can clearly be seen in the cluster (1) to which a cut has been made.

FIG. 3: FIG. 3a shows a section of stalk without treatment in which the normal structure of the stalk can be seen. In FIG. 3b the globules can be seen that are created on regenerating the wound, the large amount of capillaries contained can be seen.

EXAMPLE

A comparative trial was carried out using two sections of a greenhouse to which the same conditions were applied with the exception of the cut to the floral branch. An autumn tomato cultivated in a greenhouse was used, the "Brillante" variety (Hazera Spain 90). Thirty-five days after having planted the tomatoes the cuts were started on the experimental section, and the control section was left without modification.

Two and one half months later the tomatoes were harvested and certain properties of the crops were measured: productions (kg/m$^2$), branches per plant, percentage of fruit calibre (very big, big, medium and small), the percentage of non-marketable fruit, average sale price (€/kg) (the greater the quality the greater the sale price), net increase (gross increase—production costs), gross increase (percentage difference of production between the control section and the experimental section); as can be seen in Table 1.

TABLE 1

| Parameter | Control | Experimental |
|---|---|---|
| Production (kg/m$^2$) | 9.42 | 11.26 |
| Branches/plant | 8 | 8 |
| Very big fruit | 12% | 19% |
| Big fruit | 56% | 70% |
| Medium fruit | 28% | 10% |
| Small fruit | 2% | 0% |
| Non-marketable fruit | 2% | 1% |
| Average sale price (€/kg) | 0.46 | 0.54 |
| Net increase | | 25% |
| Gross increase | | 41% |

As can be seen in the table, there is an increase in the proportion of big fruit and the consequent reduction of small fruit. An increase of around 20% can be seen in the production per unit of surface area of cultivation.

The invention claimed is:

1. A method of improved cultivation for fruit production comprising applying pressure to the capillary sap ducts at the base of the floral cluster sufficient to damage a limited number of said ducts during inflorescence, such that regeneration and an increase in number of said ducts is effected to increase sap flow to the developing fruit.

2. The method of cultivation of fruit crops according to claim 1, wherein the pressure is made a short time after the appearance of first flowers.

3. The method of cultivation of fruit crops according to claim 1, wherein the pressure is applied to the Solanaceae group.

4. The method of cultivation of fruit crops according to claim 1, wherein the pressure is applied by making it in the period between the opening of first flowers and the end of a fattening of last fruit in order to thus obtain bigger fruit.

* * * * *